US009156758B2

(12) United States Patent
Singh

(10) Patent No.: US 9,156,758 B2
(45) Date of Patent: Oct. 13, 2015

(54) PERFLUOROALKYLATION OF CARBONYL COMPOUNDS

(71) Applicant: Rajendra P. Singh, Broomfield, CO (US)

(72) Inventor: Rajendra P. Singh, Broomfield, CO (US)

(73) Assignee: CoorsTek Fluorochemicals, Inc., Arvada, CO (US)

(*) Notice: Subject to any disclaimer, the term of this patent is extended or adjusted under 35 U.S.C. 154(b) by 18 days.

(21) Appl. No.: 14/137,078

(22) Filed: Dec. 20, 2013

(65) Prior Publication Data

US 2015/0218068 A1 Aug. 6, 2015

(51) Int. Cl.
*C07C 29/64* (2006.01)
*C07C 45/63* (2006.01)

(52) U.S. Cl.
CPC ............... *C07C 29/64* (2013.01); *C07C 45/63* (2013.01)

(58) Field of Classification Search
CPC .............................. C07C 29/64; C07C 45/63
USPC .................................. 568/322, 364; 556/463
See application file for complete search history.

(56) References Cited

PUBLICATIONS

Kim et al., "The first Cu(I)-mediated nucleophilic trifluoromethylation reactions using (trifluoromethyl)trimethylsilane in ionic liquids," Org. Biomol. Chem., 2, 2728-2734, 2004.*
Hagiwara et al., "A Highly Conductive Room Temperature Molten Fluoride: EMIF-2.3HF," Journal of the Electrochemical Society, 149(1), D1-D4, 2002.*
Marsh et al., "Room temperature ionic liquids and their mixtures—a review," Fluid Phase Equilibria, 219, 93-98, 2004.*
Singh et al., "Cesium Fluoride Catalyzed Trifluoromethylation of Esters, Aldehydes, and Ketones with (Trifluoromethyl)trimethylsilane," Journal of Organic Chemistry, 64, 2873-2876, 1999.*
Begue, J-P. et al., "Prepration of Trifluoromethyl Ketones and Related Fluorinated Ketones," Tetrahedron, 1991, V. 47, pp. 3207-3258.
Singh, R.P. et al., "Cesium Fluoride Catalyzed Trifluoromethylation of Esters, Aldehydes, and Ketones with (Trifluoromethyl)trimethylsilane," J. Org. Chem., 1999, 64, 2873-2876.
Sevenard, D.V. et al., "2-Trifluoromethyl-1,3-dithianylium triflate: a convenient 'masked' electrophilic pentafluoroethylation reagent," Tet. Lett., 2003, 44, 5995-5998.
Prakash, G.K.S. et al., "Perfluoroalkylation with Organosilicon Reagents," Chem. Rev., 1997, 97, 757-786.
Petrov, V.A., "Reaction of polyfluorinated imines with trifluoromethyltrimethylsilane. Direct synthesis of N-(perfluorot-butyl)amines," Tet. Lett., 2000, 41, 6959-6963.
Nelson, D.W. et al., "alpha-(Trifluoromethyl)amine Derivatives via Nucleophilic Trifluoromethylation of Nitrones," J. Org. Chem., 2001, 66, 2572-2582.
Li, N.-S. et al., "2'-C-Branched Ribonucleosides. 2. Synthesis of 2'-C-beta-Trifluoromethyl Pyrimidine Ribonucleosides," Org. Lett., 2001, 3, 1025-1028.
Lin, P. et al., "Synthesis of Monotrifluoromethyl-Substituted Saturated Cycles," Tetrahedron, 2000, 56, 3635-3671.
Keumi, T. et al., "A Convenient Trifluoroacetylation of Arenes with 2-(Trifluoroacetoxy)pyridine," Chem. Lett., 1990, 783-786.
Cockburn, W.F. et al., "The Reaction of Acetic and Trifluoroacetic Anhydrides with some Substituted Guanidine Hydrochlorides," Can. J. Chem., 1957, 35, 1285-1292.
Benayoud, F. et al., "Trifluoromethyl ketones derived from squalene: inhibition of the cholesterol biosynthesis in HepG2 cells," Tet. Lett., 2000, 41, 6367-6370.
Singh, R.P. et al., "CsF-Catalyzed Nucleophilic Trifluoromethylation of trans-Enones with Trimethyl(trifluoromethyl) silane: A Facile Synthesis of trans-alpha-Trifluoromethyl Allylic Alcohols," Org. Lett., 1999, 1, 1047-1049.
Singh, R. P. et al., "Nucleophilic Trifluoromethylation Reactions of Organic Compounds with (Trifluoromethyl) trimethylsilane," 2000, 56, 7613-7632.
Krishnamurti, R. et al., "Preparation of Trifluoromethyl and Other Periuoroalkyl Compounds with (Perfluoralkyl) trimethylsilanes," J. Org. Chem., 1991, 56, 984-989.
Wiedemann, J. et al., "Direct Preparation of Trifluoromethyl Ketones from Carboxylic Esters: Trifluoromethylation with (Trifluoromethyl)trimethylsilane," Angew, Chem. Int. Ed., 1998, 37, 820-821.
Theodora W. Greene and Peter G. M. Wuts, "Protective Groups in Organic Synthesis", Book, 1999, Third Edition, John Wiley & Sons, Inc., New York, United States.
Ian T. Harrison and Shuyen Harrison, "Compendium of Organic Synthetic Methods", Book, 1971, John Wiley & Sons, Inc., New York, United States.
Yasuo Yokoyama, "Chemoselective Trifluoromethylation of Methyl Esters Using an Et3GeNa/C6H5SCF3 Combination: Efficient Synthesis of Trifluoromethyl Ketones", Journal Article, Aug. 1997, pp. 907-908.

* cited by examiner

*Primary Examiner* — Paul A Zucker
*Assistant Examiner* — Mark Luderer
(74) *Attorney, Agent, or Firm* — Don D. Cha; Hamilton DeSanctis & Cha, LLP

(57) ABSTRACT

The present invention provides a process for producing a compound comprising a perfluorinated alkyl group moiety from a carbonyl compound. Typically, the process includes contacting a carbonyl compound with a silane compound in the presence of a fluorohydrogenate ionic liquid under conditions sufficient to produce a compound comprising a perfluorinated alkyl group. The silane compound includes a perfluoroalkyl group.

18 Claims, No Drawings

PERFLUOROALKYLATION OF CARBONYL COMPOUNDS

FIELD OF THE INVENTION

The present invention relates to a process for producing a compound comprising a perfluoroalkyl group. In one particular embodiment, the process is catalyzed by a fluorohydrogenate ionic liquid as catalyst and utilizes a perfluoroalkyltrimethylsilane as a perfluoroalkylating reagent.

BACKGROUND OF THE INVENTION

Fluorine is the element with highest electronegativity. Due to its size and unique electronic properties, fluorine quite often imparts significantly different (often beneficial) properties to organic molecules. (Chambers 2004; Kirsch 2004) Typically, incorporation of fluorine into molecules results in profound changes in physical and chemical properties of molecules. Fluororganics (i.e., organic compounds with one or more fluoro substituents) have important applications in a wide variety of fields including, but not limited to, material science, agricultural chemistry and the pharmaceutical industry. (Liebman, Greenberg, and Dolbier 1988).

Significant work has been carried out in the past to incorporate a fluorinated moiety in organic molecules. Trifluoromethyltrimethylsilane (TMS-CF$_3$) is a well known trifluoromethylating reagent. Usefulness of TMS-CF$_3$ has been extensively demonstrated by introducing trifluoromethyl group to transform aldehydes and ketones to trifluoromethylated alcohols. Introducing the trifluoromethyl group at various carbon, sulfur, phosphorus and nitrogen centers has been also demonstrated. (Prakash and Yudin 1997; Singh and Shreeve 2000).

Various fluoride sources, such as tetrabutylammonium fluoride (TBAF), tetrabutylammonium triphenyldifluorosilicate (TBAT), tetramethylammonium fluoride (TMAF) or cesium fluoride, have been used as a catalyst (or initiator) for the trifluoromethylation reaction of different electrophiles. (Singh and Shreeve 2000; Nelson, Owens, and Hiraldo 2001; Petrov 2000; Li, Tang, and Piccirilli 2001; Sevenard et al. 2003; Benayoud et al. 2000; Lin and Jiang 2000). However, these initiators are expensive and moisture sensitive. The most commonly used catalyst for trifluoromethylation using TMS-CF$_3$ is tetrabutylammonium fluoride (TBAF) which typically exists in a hydrated form, e.g., as a trihydrate. TBAF is also available commercially as 1 M solution in THF. Such a solution typically has about 5% water. Attempts to dehydrate TBAF further at higher temperature often leads to production of HF and olefinic byproducts. Without being bound by any theory, it is believed that the presence of water facilitates decomposition of TMSCF$_3$ into CF$_3$H, thereby resulting in a significantly lower or no desired reaction.

Conventional methods for converting simple esters into the corresponding trifluoromethyl ketones are a relatively slow or sluggish process or often results in a low yield of the desired product. The main reason of this failure is the presence of water in the catalyst (TBAF). It is believed that water destroys the key intermediate formed during the reaction, thereby interfering in the catalytic cycle.

Therefore, there is a continuing need for fluorination catalyst or initiator for perfluoroalkylation reaction of organic compounds.

SUMMARY OF THE INVENTION

Some aspects of the invention provide a method for producing a compound comprising a perfluorinated alkyl group moiety from a carbonyl compound. Typically, such a method includes contacting a carbonyl compound with a silane compound comprising a perfluoroalkyl group (i.e., —C$_n$F$_{2n+1}$) in the presence of a fluorohydrogenate ionic liquid under conditions sufficient to produce a compound comprising a perfluorinated alkyl group.

In some embodiments, the carbonyl compound is an aldehyde, a ketone, or an ester.

Still in other embodiments, the silane compound is a perfluoroalkyl(trialkyl)silane compound.

Yet in other embodiments, said fluorohydrogenate ionic liquid comprises a quaternary ammonium cation. Typically, said quaternary ammonium cation comprises a nitrogen-heteroaryl cation. In some instances, said quaternary ammonium cation comprises N-ethyl-N-methylimidazolium, N-methyl-N-propylpyrrolidinium, N-methyl-N-butylpyrrolidinium or a combination thereof.

Still in other embodiments, the amount of said fluorohydrogenate ionic liquid used in the process is less than 1 equivalent relative to the amount of said carbonyl compound.

Other aspects of the invention provide a process for producing a siloxy compound of the formula:

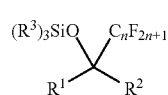

I comprising contacting a carbonyl compound of the formula:

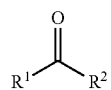

II with a silyl compound of the formula:

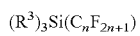

III in the presence of a fluorohydrogenate ionic liquid under conditions sufficient to produce a siloxy compound of Formula I,
wherein
n is an integer from 1 to 30;
R$^1$ is hydrogen, alkyl, cycloalkyl, heterocycloalkyl, aryl, heteroaryl, haloalkyl, heteroalkyl, (cycloalkyl)alkyl, (heterocycloalkyl)alkyl, aralkyl or heteroaralkyl;
R$^2$ is hydrogen, alkyl or a moiety of the formula —OR$^4$, wherein R$^4$ is alkyl, cycloalkyl, heterocycloalkyl, aryl, heteroaryl, haloalkyl, heteroalkyl, (cycloalkyl)alkyl, (heterocycloalkyl)alkyl, aralkyl or heteroaralkyl; and
each of R$^3$ is independently alkyl, cycloalkyl, aryl, (cycloalkyl)alkyl or aralkyl.

In some embodiments, R$^2$ is a moiety of the formula —OR$^4$. Within these embodiments, in some instances the process further comprises the step of hydrolyzing said siloxy compound of Formula I to produce a ketone compound of the formula:

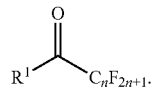

Yet in other embodiments, each of $R^3$ is independently $C_1$-$C_6$ alkyl. Within these embodiments, in some instances, $R^3$ is methyl.

Still in other embodiments, said fluorohydrogenate ionic liquid comprises a quaternary ammonium cation. Within these embodiments, in some instances said quaternary ammonium cation comprises a nitrogen-heteroaryl cation. In some particular instances, said quaternary ammonium cation comprises N-ethyl-N-methylimidazolium, N-methyl-N-propylpyrrolidinium, N-methyl-N-butylpyrrolidinium or a combination thereof.

In other embodiments, $R^2$ is hydrogen or alkyl. In these embodiments, in some instances the process further comprises the steps of hydrolyzing said siloxy compound of Formula I to produce an alcohol compound of the formula:

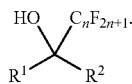

Yet still in other embodiments, the amount of said fluorohydrogenate ionic liquid used in the process is less than 1 equivalent relative to the amount of said carbonyl compound of Formula II. Within these embodiments, in some instances, the amount of said fluorohydrogenate ionic liquid used in the process ranges from about 0.2 to 0.4 equivalent relative to the amount of said carbonyl compound of Formula II.

Still yet in other embodiments, the amount of said silyl compound of Formula III used in the process is at least 1 equivalent relative to the amount of said carbonyl compound of Formula II.

DETAILED DESCRIPTION OF THE INVENTION

Definitions

"Alkyl" refers to a saturated linear monovalent hydrocarbon moiety of one to twelve, typically one to six, carbon atoms or a saturated branched monovalent hydrocarbon moiety of three to twelve, typically three to six, carbon atoms. Exemplary alkyl group include, but are not limited to, methyl, ethyl, n-propyl, 2-propyl, tert-butyl, pentyl, and the like.

"Alkylene" refers to a saturated linear divalent hydrocarbon moiety of one to twelve, typically one to six, carbon atoms or a branched saturated divalent hydrocarbon moiety of three to twelve, typically three to six, carbon atoms. Exemplary alkylene groups include, but are not limited to, methylene, ethylene, propylene, butylene, pentylene, and the like.

"Aryl" refers to a monovalent mono-, bi- or tricyclic aromatic hydrocarbon moiety of 6 to 15 ring atoms which is optionally substituted with one or more substituents. When the aryl group is substituted, it is typically substituted with one, two, or three substituents, often one substituent, within the ring structure. When two or more substituents are present in an aryl group, each substituent is independently selected. Exemplary substituents of aryl group include, but are not limited to, alkyl, halo, haloalkyl, cyano, nitro, amino, monoalkyl amino, dialkylamino, —$OR^a$ (where $R^a$ is hydrogen or alkyl), etc.

"Aralkyl" refers to a moiety of the formula —$R^bR^c$ where $R^b$ is an alkylene and $R^c$ is an aryl group as defined herein. Exemplary aralkyl groups include, but are not limited to, benzyl, phenylethyl, and the like.

"Cycloalkyl" refers to a non-aromatic, typically saturated, monovalent mono- or bicyclic hydrocarbon moiety of three to ten ring carbons. The cycloalkyl can be optionally substituted with one or more substituents. When substituted, the cycloalkyl typically comprises one, two, or three substituents within the ring structure. When two or more substituents are present in a cycloalkyl group, each substituent is independently selected. Cycloalkyl can also include one or more unsaturation (e.g., olefinic and/or acetylenic) moieties. Exemplary cycloalkyls include cyclopropyl, cyclobutyl, cyclopentyl, cyclohexyl, cyclooctyl groups and the like. Exemplary substituents for cycloalkyl group include, but are not limited to, alkyl, haloalkyl, halo, heteroalkyl, aryl, —$OR^a$ (where $R^a$ is hydrogen or alkyl) and the like.

The terms "cycloalkylalkyl" and "(cycloalkyl)alkyl" are used interchangeably herein and refer to a moiety of the formula —$R^dR^e$ where $R^d$ is an alkylene group and $R^e$ is a cycloalkyl group as defined herein. Exemplary cycloalkylalkyl groups include, but are not limited to, cyclopropylmethyl, cyclohexylpropyl, 3-cyclohexyl-2-methylpropyl, cyclohexylmethyl, and the like.

The term "fluorohydrogenate ionic liquid" refers to an ionic liquid comprising one or more fluorohydrogenate anions. Typically, fluorohydrogenate anion is of the form $F^-.2HF$ or $F^-.3HF$, i.e., a fluoride anion that is solvated with one or more, typically two or three hydrogen fluoride. Typically, fluorohydrogenate ionic liquids have melting points below 100° C. and are often a liquid at room temperature. Fluorohydrogenate ionic liquids are typically vacuum-stable and sometimes have an empirical formula $F^-.2.3HF$. Typical members of the fluorohydrogenate ionic liquid family include a quaternary ammonium cation. Often, the quaternary ammonium cation comprises a nitrogen-heteroaryl cation. Exemplary fluorohydrogenate ionic liquids include, but are not limited to, N-methyl-N-butylpyrrolidinium fluorohydrogenate ("PYR$_{14}$F(HF)$_{2.3}$"), N-methyl-N-propylpyrrolidinium fluorohydrogenate ("PYR$_{13}$F(HF)$_{2.3}$"), and N-ethyl-N-methylimidazolium fluorohydrogenate ("EMIMF(HF)$_{2.3}$").

The terms "halo," "halogen" and "halide" are used interchangeably herein and refer to fluoro, chloro, bromo, or iodo.

"Haloalkyl" refers to an alkyl group as defined herein in which one or more hydrogen atom is replaced by same or different halo atoms. The term "haloalkyl" also includes perhalogenated alkyl groups in which all alkyl hydrogen atoms are replaced by halogen atoms. Exemplary haloalkyl groups include, but are not limited to, —$CH_2Cl$, —$CF_3$, —$CH_2CF_3$, —$CH_2CCl_3$, and the like.

"Heterocycloalkyl" means a non-aromatic monocyclic moiety of three to eight ring atoms in which one or two ring atoms are heteroatoms selected from N, O, or $S(O)_n$ (where n is an integer from 0 to 2), the remaining ring atoms being C, where one or two C atoms can optionally be a carbonyl group. The heterocycloalkyl ring can be optionally substituted independently with one or more substituents. When two or more substituents are present in a heterocycloalkyl group, each substituent is independently selected. Exemplary substituents for heterocyclyl group include, but are not limited to, alkyl, haloalkyl, heteroalkyl, halo, aryl and the like.

The term "(heterocycloalkyl)alkyl" refers to a moiety of the formula —$R^fR^g$ where $R^f$ is alkylene and $R^g$ is heterocycloalkyl as defined herein.

The term "heteroaryl" refers to a monovalent monocyclic or bicyclic aromatic moiety of 5 to 12 ring atoms containing one, two, or three ring heteroatoms selected from N, O, or S, the remaining ring atoms being C. The heteroaryl ring is optionally substituted independently with one or more substituents. Exemplary substituents for heteroaryl include those of aryl groups and the like. Exemplary heteroaryl includes, but is not limited to, pyridyl, furanyl, thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, and the like.

The term "heteroaralkyl" refers to a moiety of the formula —$R^h R^i$ where $R^h$ is alkylene and $R^i$ is heteroaryl as defined herein.

As used herein, the term "heteroalkyl" means a branched or unbranched, cyclic or acyclic saturated alkyl moiety containing carbon, hydrogen and one or more heteroatoms in place of a carbon atom, or optionally one or more heteroatom-containing substituents independently selected from =O, —$OR^a$, —$C(O)R^a$, —$NR^b R^c$, —$C(O)NR^b R^c$ and —$S(O)_n R^d$ (where n is an integer from 0 to 2). $R^a$ is hydrogen, alkyl, haloalkyl, cycloalkyl, cycloalkylalkyl, heterocyclyl, heterocyclylalkyl, aryl, aralkyl, heteroaryl, heteroaralkyl, or acyl. $R^b$ is hydrogen, alkyl, haloalkyl, cycloalkyl, cycloalkylalkyl, heterocyclyl, heterocyclylalkyl, aryl, aralkyl, heteroaryl, heteroaralkyl, or acyl. $R^c$ is hydrogen, alkyl, haloalkyl, cycloalkyl, cycloalkylalkyl, heterocyclyl, heterocyclylalkyl, aryl, aralkyl, acyl, alkylsulfonyl, carboxamido, or mono- or di-alkylcarbomoyl. Optionally, $R^b$ and $R^c$ can be combined together with the nitrogen to which each is attached to form a four-, five-, six- or seven-membered heterocyclic ring (e.g., a pyrrolidinyl, piperidinyl or morpholinyl ring). $R^d$ is hydrogen (provided that n is 0), alkyl, haloalkyl, cycloalkyl, cycloalkylalkyl, heterocyclyl, heterocyclylalkyl, aryl, aralkyl, heteroaryl, heteroaralkyl, acyl, amino, monosubstituted amino, disubstituted amino, or hydroxyalkyl. Representative examples include, for example, 2-methoxyethyl, benzyloxymethyl, thiophen-2-ylthiomethyl, 2-hydroxyethyl, and 2,3-dihydroxypropyl.

"Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

When describing a chemical reaction, the terms "treating", "contacting" and "reacting" are used interchangeably herein, and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the terms "those defined above" and "those defined herein" when referring to a variable incorporates by reference the broad definition of the variable as well as any narrow and/or narrower definitions, if any.

Methods and Processes of the Invention

Nucleophilic perfluoroalkylation reactions of organic compounds using perfluoroalkyltrimethylsilane is an excellent way to introduce perfluoroalkyl groups. The bond between Si and $C_n F_{2n+1}$ in perfluoroalkyltrimethylsilane ($Me_3Si$—$C_n F_{2n+1}$) is weak due to the highly electron-withdrawing nature of the perfluoroalkyl group. It is easily cleaved by fluoride ions to produce $Me_3SiF$ and to liberate perfluoroalkyl anion (i.e., $C_n F_{2n+1}^-$) as a nucleophile.

Unfortunately, as discussed above, conventional methods for introducing a perfluoroalkyl group using a perfluoroalkyltrimethylsilane is a relatively slow or sluggish process or often results in a low yield of the desired product. In particular, conventional catalysts and/or initiators are hygroscopic thereby rendering conventional methods unsuitable in many instances.

The present inventors have discovered that many of the deficiencies of conventional methods for introducing a perfluoroalkyl group can be readily overcome by utilizing a fluorohydrogenate ionic liquid. A wide variety of compounds can be perfluoroalkylated using the process of the invention. Some of the compounds that can be perfluoroalkylated include carbonyl compounds (i.e., compounds comprising a C=O functional group), such as ketones, aldehydes and esters, and sulfonate compounds, sulfinic compounds and selenate compounds.

In some embodiments, as illustrated in Scheme 1, the invention provides a simple, one-step process for perfluoroalkylating carbonyl compounds such as esters, aldehydes and ketones. Typically, reacting the carbonyl compound with a perfluoroalkyltrimethylsilane of the general formula $(CH_3)_3Si$—$C_n F_{2n+1}$ in the presence of a fluorohydrogenate ionic liquid, such as $EMIMF(HF)_{2.3}$, $PYR_{14}F(HF)_{2.3}$, $PYR_{13}F(HF)_{2.3}$ or a combination thereof. Often, the fluorohydrogenate ionic liquid is used as a catalyst. A typical amount of fluorohydrogenate ionic liquid used in processes of the invention is less than 1 equivalent, often about 0.5 equivalent or less, more often about 0.2 to 0.4 equivalent, and most often 0.1 equivalent or less relative to the amount of carbonyl compound.

SCHEME 1

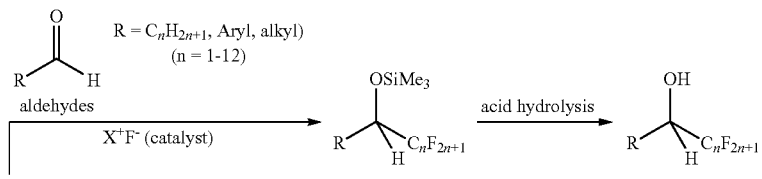

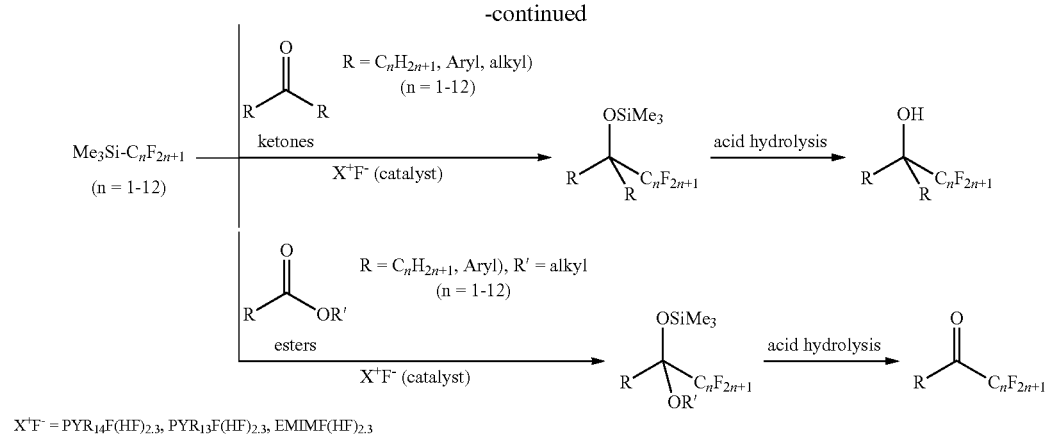

$X^+F^- = PYR_{14}F(HF)_{2.3}, PYR_{13}F(HF)_{2.3}, EMIMF(HF)_{2.3}$

Referring again to Scheme 1, the reaction typically produces a silyl ether intermediate. This silyl ether can be isolated or it can be converted to the corresponding alcohol or ketone in situ or during work-up process.

When the carbonyl compound is an aldehyde, e.g., RCHO (where R is hydrogen, alkyl, cycloalkyl, heterocycloalkyl, aryl, heteroaryl, haloalkyl, heteroalkyl, (cycloalkyl)alkyl, (heterocycloalkyl)alkyl, aralkyl or heteroaralkyl), the product produced by processes of the invention is a perfluoroalkylated silyl ether or alcohol of the formula $R(C_nF_{2n+1})CH(OR')$, where n is typically an integer from 1 to 8 and R' is hydrogen or trialklylsilyl group such as trimethylsilyl.

When the carbonyl compound is a ketone, such as R'COR" (where each of R' and R" is independently alkyl, cycloalkyl, heterocycloalkyl, aryl, heteroaryl, haloalkyl, heteroalkyl, (cycloalkyl)alkyl, (heterocycloalkyl)alkyl, aralkyl or heteroaralkyl), the resulting product is a silyl ether or a corresponding alcohol of the formula $R'(C_nF_{2n+1})CR"(OR)$, where n is typically an integer from 1 to 8 and R is hydrogen or trialkylsilyl group such as trimethylsilyl.

When the carbonyl compound is an ester, such as $RCO_2R'$ (where R is hydrogen, alkyl, cycloalkyl, heterocycloalkyl, aryl, heteroaryl, haloalkyl, heteroalkyl, (cycloalkyl)alkyl, (heterocycloalkyl)alkyl, aralkyl or heteroaralkyl and R' is alkyl, cycloalkyl, heterocycloalkyl, aryl, heteroaryl, haloalkyl, heteroalkyl, (cycloalkyl)alkyl, (heterocycloalkyl) alkyl, aralkyl or heteroaralkyl), the resulting intermediate can be converted to the corresponding perfluoroalkyl ketone compound of the formula $R(C_nF_{2n+1})C=O$, where n is an integer typically from 1 to 8.

The carbonyl compound can also include other functional group(s) as long as such functional groups are either relatively non-reactive under the reaction condition or are protected. For example, an amino ester, such as $R_2N(CH_2)_mCO_2R'$ (where each of R is alkyl or aryl, m is an integer from 1 to 6, and R' is alkyl, cycloalkyl, heterocycloalkyl, aryl, heteroaryl, haloalkyl, heteroalkyl, (cycloalkyl) alkyl, (heterocycloalkyl)alkyl, aralkyl or heteroaralkyl) can be converted to the corresponding perfluoroalkylated compound of the formula $R_2N(CH_2)_m(C_nF_{2n+1})C=O$, where n is typically an integer from 1 to 8.

Other compounds that can be perfluoroalkylated include sulfonic esters (e.g., R'—$SO_2$—OR"), sulfinic esters (e.g., R'—SO—OR"), and selenic ester (e.g., R'—SeO—OR") (where R' is hydrogen, alkyl, cycloalkyl, heterocycloalkyl, aryl, heteroaryl, haloalkyl, heteroalkyl, (cycloalkyl)alkyl, (heterocycloalkyl)alkyl, aralkyl or heteroaralkyl and R" is alkyl, cycloalkyl, heterocycloalkyl, aryl, heteroaryl, haloalkyl, heteroalkyl, (cycloalkyl)alkyl, (heterocycloalkyl) alkyl, aralkyl or heteroaralkyl. Typically R' is alkyl, cycloalkyl, heterocycloalkyl, aryl, heteroaryl, haloalkyl, heteroalkyl, (cycloalkyl)alkyl, (heterocycloalkyl)alkyl, aralkyl or heteroaralkyl). The resulting products of these compounds are, respectively, of the formula R—$SO_2(C_nF_{2n+1})$, R—S (O)—$(C_nF_{2n+1})$, and R—Se(O)—$(C_nF_{2n+1})$, where n is typically an integer from 1 to 8.

The reaction temperature can vary depending on a variety of factors such as, but not limited to, the reactivity of the carbonyl (or sulfonate, sulfinate or selenate) compound, the amount of perfluoroalkylating silane compound used, the amount and the nature of the fluorohydrogenate ionic liquid used, the solvent used, the reaction time, etc. However, a typical reaction temperature ranges from about −78° C. to about 50° C., typically from about −40° C. to about 30° C. and often from about −10° C. to about 25° C. Generally, the reaction is carried out at 0° C. to room temperature.

The yield of the silyl ether intermediate or the final product can also vary depending on a wide variety of factors such as those describe above. Typically, the yield of the product is at least 80%, often at least 90%, and more often at least 95%. Such a yield is a significantly higher when compared to conventional methods.

The reaction time can vary greatly depending on a variety factors such as those discussed above. In addition, the concentration of the reactants can also influence the reaction time. Typically, however, the reaction time ranges from about 1 h to about 24 h, often from about 1 h to about 12 h, and more often from about 1 h to about 6 h.

When a perfluoroalkyltrimethyl silane is used as a perfluoroalkylating compound, the reaction also produces trimethylsilylfluoride. This product can be recovered and recycled.

Usefulness of organic compound comprising a perfluoroalkyl group is well known to one skilled in the art. For example, trifluoromethyl ketones are known to be potential inhibitors of hydrolytic enzymes because of their ability to form stable hydrates (Gelb, Svaren, and Abeles 1985). Prior to the discovery by the present inventors, typical methods for the synthesis of trifluoromethyl ketones were rare and involved multistep synthetic operations (Begue and Bonnet-Delpon 1991) (Yokoyama and Mochida 1997; Keumi et al. 1990; Cockburn and Bannard 1957).

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

All the reactions were carried out under anhydrous argon atmosphere. All the fluorohydrogenate ionic liquids used here were synthesized using anhydrous HF under anhydrous conditions.

EXAMPLE 1

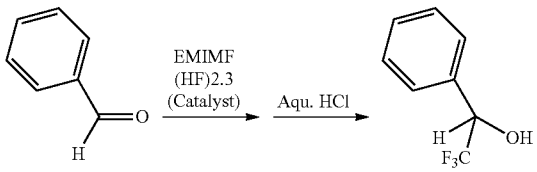

Anhydrous benzaldehyde (1.06 mg, 10 mmol) and (trifluoromethyl)trimethylsilane (1.46 g, 10.25 mmol) were placed in a dried flask under argon and dissolved in 10 ml of dichloromethane. The resulting solution was cooled with an ice-water bath. A catalytic amount of EMIM F(HF)$_{2.3}$ (35 mg, 0.2 mmol) was added while the reaction mixture was stirred. Some gas evolution (Me$_3$SiF) was observed. After 0.5 h stirring, ice-water bath was removed and stirred at room temperature for additional 2.5 h. The reaction mixture was then quenched with 4 N hydrochloric acid (10 ml) and was stirred at room temperature for 1 h. The resulting solution was diluted with another 5 ml of dichloromethane and aqueous phase was removed. The organic layer was washed with 10 ml of water and concentrated to yield the desired product. Yield: 1.62 g, Yield: 92%. Fluorine nmr in CDCl$_3$ showed a doublet at −76.6 ppm assigned for CF$_3$ with $J_{F-H}$=7.0 Hz.

EXAMPLE 2

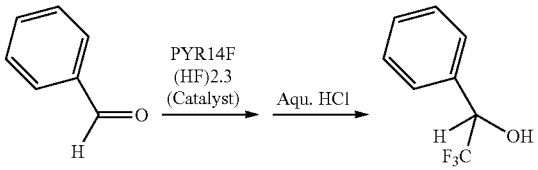 [SMILES: O=Cc1ccccc1 ; OC(c1ccccc1)C(F)(F)F]

Anhydrous benzaldehyde (1.06 mg, 10 mmol) and (trifluoromethyl)trimethylsilane (1.46 g, 10.25 mmol) were placed in a dried flask under argon and dissolved in 10 ml of dichloromethane. The resulting solution was cooled with an ice-water bath. A catalytic amount of methylbutylpyrrolidinium fluorohydrogenate ("PYR$_{14}$F(HF)$_{2.3}$") (41.4 mg, 0.2 mmol) was added to the mixture. Some gas evolution (Me$_3$SiF) was seen. After 0.5 h stirring, the ice-water bath was removed and the mixture was stirred at room temperature for additional 2.5 h. The reaction was then quenched with 4 N hydrochloric acid (10 ml) and stirred at room temperature for 1 h. The resulting mixture was diluted with 5 ml of dichloromethane and the aqueous phase was removed. The organic layer was washed with 10 ml of water and concentrated to yield the desired product. Yield: 1.58 g, Yield: 90%. Fluorine nmr in CDCl$_3$ showed a doublet at −76.6 ppm assigned for CF$_3$ with $J_{F-H}$=7.0 Hz.

EXAMPLE 3

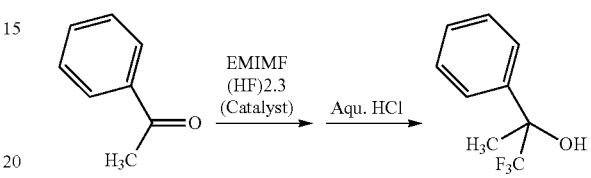

Anhydrous acetophenone (1.20 g, 10 mmol) and (trifluoromethyl)trimethylsilane (1.46 g, 10.25 mmol) were placed in a dried flask under argon and dissolved in 10 ml of dichloromethane. The mixture was cooled with an ice-water bath. A catalytic amount of EMIMF(HF)$_{2.3}$ (35 mg, 0.2 mmol) was added. Some gas evolution (Me$_3$SiF) was seen. After 0.5 h stirring, the ice-water bath was removed and the mixture was stirred at room temperature for additional 2.5 h. The reaction was quenched by adding 4 N hydrochloric acid (10 ml), and the resulting solution was stirred at room temperature for 1 h and diluted with 5 ml of dichloromethane. The aqueous phase was removed. The organic layer was washed with 10 ml of water and concentrated to yield the desired product. Yield: 1.78 g, Yield: 94%. Fluorine nmr in CDCl$_3$ showed a singlet at −81.7 ppm assigned for CF$_3$.

EXAMPLE 4

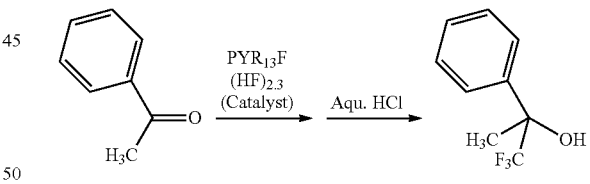

Anhydrous acetophenone (1.20 g, 10 mmol) and (trifluoromethyl)trimethylsilane (1.46 g, 10.25 mmol) were placed in a dried flask under argon and dissolved in 10 ml of dichloromethane. The resulting solution was cooled with an ice-water bath. A catalytic amount of PYR$_{13}$F(HF)$_{2.3}$ (38 mg, 0.2 mmol) was added. Some gas evolution (Me$_3$SiF) was seen. After 0.5 h stirring, the ice-water bath was removed, and the mixture was stirred at room temperature for additional 2.5 h. The reaction was quenched by adding 4 N hydrochloric acid (10 ml), and the resulting solution was stirred at room temperature for 1 h and diluted with 5 ml of dichloromethane. The aqueous phase was removed. The organic layer was washed with 10 ml of water and concentrated to yield the desired product. Yield: 1.72 g, Yield: 91%. Fluorine nmr in CDCl$_3$ showed a singlet at −81.7 ppm assigned for CF$_3$.

EXAMPLE 5

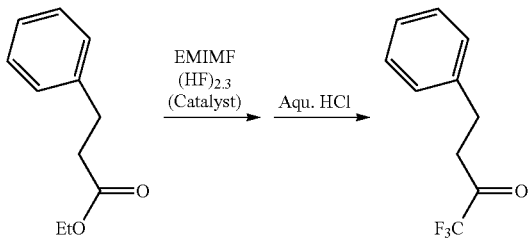 [SMILES: CCOC(=O)CCc1ccccc1 ; O=C(CCc1ccccc1)C(F)(F)F]

Anhydrous ethyl hydrocinnamate (1.78 g, 10 mmol) and (trifluoromethyl)-trimethylsilane (1.46 g, 10.25 mmol) were placed in a dried flask under argon and dissolved in 10 ml of dichloromethane. The resulting solution was cooled with and ice-water bath. A catalytic amount of EMIMF(HF)$_{2.3}$ (35 mg, 0.2 mmol) was added. Some gas evolution (Me$_3$SiF) was seen. After 0.5 h stirring, the ice-water bath was removed and the mixture was stirred at room temperature for additional 5 h. The reaction was quenched by adding 4 N hydrochloric acid (10 ml), and the resulting mixture was stirred at room temperature for 1 h. The mixture was diluted with 5 ml of dichloromethane and the aqueous phase was removed. The organic layer was washed with 10 ml of water and concentrated to yield the desired product. Yield: 1.76 g, Yield: 87%. Fluorine nmr in CDCl$_3$ showed a singlet at −80.2 ppm assigned for CF$_3$.

EXAMPLE 6

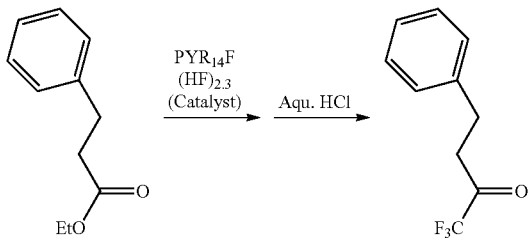 [SMILES: CCOC(=O)CCc1ccccc1 ; O=C(CCc1ccccc1)C(F)(F)F]

Anhydrous ethyl hydrocinnamate (1.78 g, 10 mmol) and (trifluoromethyl)-trimethylsilane (1.46 g, 10.25 mmol) were placed in a dried flask under argon and dissolved in 10 ml of dichloromethane. The resulting mixture was cooled with an ice-water bath, and a catalytic amount of PYR$_{14}$F(HF)$_{2.3}$ (41.4 mg, 0.2 mmol) was added. Some gas evolution (Me$_3$SiF) was seen. After 0.5 h stirring, the ice-water bath was removed and the mixture was stirred at room temperature for additional 5 h. The reaction was quenched by adding 4 N hydrochloric acid (10 ml), and the resulting mixture was stirred at room temperature for 1 h. The solution was diluted with 5 ml of dichloromethane, and the aqueous phase was removed. The organic layer was washed with 10 ml of water and concentrated to yield the desired product. Yield: 1.78 g, Yield: 88%. Fluorine nmr in CDCl$_3$ showed a singlet at −80.2 ppm assigned for CF$_3$.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A process for producing a compound comprising a perfluorinated alkyl group moiety from a carbonyl compound, said process comprising contacting a carbonyl compound with a silane compound comprising a perfluoroalkyl group in the presence of a fluorohydrogenate ionic liquid under conditions sufficient to produce a compound comprising a perfluorinated alkyl group, wherein the amount of said fluorohydrogenate ionic liquid used in the process is less than 1 equivalent relative to the amount of said carbonyl compound.

2. The process of claim 1, wherein said carbonyl compound is an aldehyde, a ketone, or an ester.

3. The process of claim 1, wherein said silane compound is a perfluoroalkyl(trialkyl)silane compound.

4. The process of claim 1, wherein said fluorohydrogenate ionic liquid comprises a quaternary ammonium cation.

5. The process of claim 4, wherein said quaternary ammonium cation comprises a nitrogen-heteroaryl cation.

6. The process of claim 4, wherein said quaternary ammonium cation comprises N-ethyl-N-methylimidazolium, N-methyl-N-propylpyrrolidinium, N-methyl-N-butylpyrrolidinium or a combination thereof.

7. A process for producing a siloxy compound of the formula:

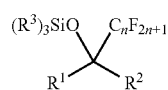

I comprising contacting a carbonyl compound of the formula:

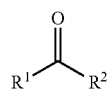

II with a silyl compound of the formula:

III in the presence of a fluorohydrogenate ionic liquid under conditions sufficient to produce a siloxy compound of Formula I,
wherein
n is an integer from 1 to 30;
R$^1$ is hydrogen, alkyl, cycloalkyl, heterocycloalkyl, aryl, heteroaryl, haloalkyl, heteroalkyl, (cycloalkyl)alkyl, (heterocycloalkyl)alkyl, aralkyl or heteroaralkyl;
R$^2$ is hydrogen, alkyl or a moiety of the formula —OR$^4$, wherein R$^4$ is alkyl, cycloalkyl, heterocycloalkyl, aryl, heteroaryl, haloalkyl, heteroalkyl, (cycloalkyl)alkyl, (heterocycloalkyl)alkyl, aralkyl or heteroaralkyl; and each of $R^3$ is independently alkyl, cycloalkyl, aryl, (cycloalkyl)alkyl or aralkyl, and wherein the amount of said fluorohydrogenate ionic liquid used in the process is less than 1 equivalent relative to the amount of said carbonyl compound of Formula II.

8. The process of claim 7, wherein $R^2$ is a moiety of the formula —$OR^4$, wherein $R^4$ is alkyl, cycloalkyl, heterocycloalkyl, aryl, heteroaryl, haloalkyl, heteroalkyl, (cycloalkyl)alkyl, (heterocycloalkyl)alkyl, aralkyl or heteroaralkyl.

9. The process of claim 8 further comprising the step of hydrolyzing said siloxy compound of Formula I to produce a ketone compound of the formula:

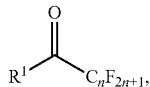

wherein n is an integer from 1 to 30.

10. The process of claim 7, wherein each of $R^3$ is independently $C_1$-$C_6$ alkyl.

11. The process of claim 10, wherein $R^3$ is methyl.

12. The process of claim 7, wherein said fluorohydrogenate ionic liquid comprises a quaternary ammonium cation.

13. The process of claim 12, wherein said quaternary ammonium cation comprises a nitrogen-heteroaryl cation.

14. The process of claim 13, wherein said quaternary ammonium cation comprises N-ethyl-N-methylimidazolium, N-methyl-N-propylpyrrolidinium, N-methyl-N-butylpyrrolidinium or a combination thereof.

15. The process of claim 7, wherein $R^2$ is hydrogen or alkyl.

16. The process of claim 15 further comprising the steps of hydrolyzing said siloxy compound of Formula I to produce an alcohol compound of the formula:

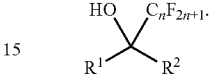

17. The process of claim 7, wherein the amount of said fluorohydrogenate ionic liquid used in the process ranges from about 0.2 to 0.4 equivalent relative to the amount of said carbonyl compound of Formula II.

18. The process of claim 7, wherein the amount of said silyl compound of Formula III used in the process is at least 1 equivalent relative to the amount of said carbonyl compound of Formula II.

* * * * *